US011786712B2

(12) United States Patent
Friedman

(10) Patent No.: US 11,786,712 B2
(45) Date of Patent: Oct. 17, 2023

(54) NITRIC OXIDE-RELEASING DEVICE

(71) Applicant: Albert Einstein College of Medicine, Bronx, NY (US)

(72) Inventor: Joel M. Friedman, West Orange, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 17/823,298

(22) Filed: Aug. 30, 2022

(65) Prior Publication Data

US 2023/0069711 A1 Mar. 2, 2023

Related U.S. Application Data

(60) Provisional application No. 63/238,521, filed on Aug. 30, 2021.

(51) Int. Cl.
*A61M 35/00* (2006.01)
*A61M 31/00* (2006.01)

(52) U.S. Cl.
CPC ............ *A61M 31/00* (2013.01); *A61M 35/30* (2019.05); *A61M 2202/0275* (2013.01)

(58) Field of Classification Search
CPC ...... A61F 13/00068; A61F 2013/00165; A61F 2013/0017; A61H 2033/0004; A61H 2033/146; A61H 33/60; A61K 38/02
See application file for complete search history.

(56) References Cited

U.S. PATENT DOCUMENTS

| | | |
|---|---|---|
| 11,484,493 B2 | 11/2022 | Friedman |
| 2004/0054313 A1 | 3/2004 | Molan |
| 2008/0057088 A1 | 3/2008 | Blass et al. |
| 2009/0297634 A1 | 12/2009 | Friedman et al. |
| 2012/0052095 A1 | 3/2012 | Chaniyilparampu et al. |
| 2014/0017121 A1 | 1/2014 | Schoenfisch et al. |
| 2014/0105986 A1 | 4/2014 | Doxey et al. |
| 2015/0147396 A1 | 5/2015 | Nacharaju et al. |
| 2017/0119814 A1 | 5/2017 | Friedman et al. |
| 2018/0256509 A1 | 9/2018 | Friedman et al. |
| 2022/0257642 A1* | 8/2022 | Munro .................... A61P 11/00 |
| 2023/0064665 A1 | 3/2023 | Friedman |
| 2023/0121214 A1 | 4/2023 | Friedman |

FOREIGN PATENT DOCUMENTS

| | | |
|---|---|---|
| WO | 2005/105059 A1 | 11/2005 |
| WO | 2009/131931 A1 | 10/2009 |
| WO | 2010/048724 A1 | 5/2010 |
| WO | 2013/169538 A1 | 11/2013 |
| WO | 2018/039752 A1 | 3/2018 |
| WO | 2020/245574 A1 | 12/2020 |

OTHER PUBLICATIONS

International Search Report and Written Opinion dated Dec. 12, 2022, in International Application No. PCT/US2022/075651, 16 pages.
Viscosity Tables, V&P Scientific, Jan. 13, 2008 (Jan. 13, 2008), 3 pages.
Karakas et al. "No-Releasing Nanoparticles Decrease Detrusor Overactivity in DNOS-/-Knockout and Transgenic Sickle Cell Mice", PD19-06, The Journal of Urology, vol. 199, No. 4S, Supplement, May 19, 2018, e397, 1 page.
Karakus et al. "NO-Releasing Nanoparticles Ameliorate Detrusor Overactivity in Transgenic Sickle Cell Mice via Restored NO/ROCK Signaling", J Pharmacol Exp Ther. May 2020;373(2):214-219. doi: 10.1124/jpet.119.264697. Epub Mar. 6, 2020., 6 pages.
Margel et al. "Nitric oxide charged catheters as a potential strategy for prevention of hospital acquired infections", PLoS One. Apr. 14, 2017; 12(4):e0174443. doi: 10.1371/journal.pone.0174443. PMID: 28410367; PMCID: PMC5391919, 17 pages.
Yang et al, 'Novel nitric oxide-generating platform using manuka honey as an anti-biofilm strategy in chronic rhinosinusitis', International Forum of Allergy & Rhinology, vol. 10, issue 2, Dec. 13, 2019 (13.21.2019), p. 223-232.
Amalraj, A. et al. "A Novel Highly Bioavailable Curcumin Formulation Improves Symptoms and Diagnostic Indicators in Rheumatoid Arthritis Patients: A Randomized, Double-Blind, Placebo-Controlled, Two-Dose, Three-Arm, and Parallel-Group Study", J Med Food. Oct. 2017;20(10):1022-1030.
Anand, P. et al. "Curcumin and cancer: an "old-age" disease with an "age-old" solution", Cancer Lett. Aug. 18, 2008;267(1):133-164.
Banez, M. J. et al. "A systemic review on the antioxidant and anti-inflammatory effects of resveratrol, curcumin, and dietary nitric oxide supplementation on human cardiovascular health", Nutr Res. Jun. 2020;78:11-26.
Babaei, F. et al. "Curcumin (a constituent of turmeric): New treatment option against COVID-19", Food Sci Nutr. Sep. 6, 2020;8(10):5215-5227.
Belcaro, G. et al. A controlled study of a lecithinized delivery system of curcumin (Meriva®) to alleviate the adverse effects of cancer treatment. Phytother Res. Mar. 2014;28(3):444-450.
Boonla, O. et al. "Curcumin improves endothelial dysfunction and vascular remodeling in 2K-1C hypertensive rats by raising nitric oxide availability and reducing oxidative stress", Nitric Oxide. Nov. 15, 2014;42:44-53.
Carter, A. "Curry compound fights cancer in the clinic", J Natl Cancer Inst. May 7, 2008;100(9):616-617.
Chen, R. et al. "Curcumin attenuates cardiomyocyte hypertrophy induced by high glucose and insulin via the PPAR?/Akt/NO signaling pathway", Diabetes Res Clin Pract. May 2015;108(2):235-242.
Choudhuri, T. et al. "Curcumin induces apoptosis in human breast cancer cells through p53-dependent Bax induction", FEBS Lett. Feb. 13, 2002;512(1-3):334-340.

(Continued)

*Primary Examiner* — Deanna K Hall
(74) *Attorney, Agent, or Firm* — Fox Rothschild LLP

(57) ABSTRACT

A device for generating nitric oxide is disclosed. The device is configured for applying to either a body cavity or a surface of a subject in need thereof. Also disclosed is a method for the treatment of diseases or conditions with the device.

21 Claims, No Drawings

(56) References Cited

OTHER PUBLICATIONS

Debata, P.R. et al. "A novel curcumin-based vaginal cream Vacurin selectively eliminates apposed human cervical cancer cells", Gynecol Oncol. Apr. 2013;129(1):145-153.

Dhandapani, K.M. et al. "Curcumin suppresses growth and chemoresistance of human glioblastoma cells via AP-1 and NFkappaB transcription factors", J Neurochem. Jul. 2007;102(2):522-538.

Dhar, S. et al. "Promising role of curcumin against viral diseases emphasizing COVID-19 management: A review on the mechanistic insights with reference to host-pathogen interaction and immunomodulation", J Funct Foods. Jul. 2021;82:104503, 12 pages.

Fang, W. et al., "The role of NO in COVID-19 and potential therapeutic strategies". Free Radic Biol Med. Feb. 1, 2021;163:153-162.

Farhangkhoee, H. et al. "Differential effects of curcumin on vasoactive factors in the diabetic rat heart", Nutr Metab (Lond). Jul. 18, 2006;3:27, 8 pages.

Forte, M. et al. "Targeting Nitric Oxide with Natural Derived Compounds as a Therapeutic Strategy in Vascular Diseases", Oxid Med Cell Longev. 2016;Article ID:7364138, 20 pages.

Hajavi, J. et al. "Curcumin: A Naturally Occurring Modulator of Adipokines in Diabetes", J Cell Biochem. Dec. 2017;118(12):4170-4182.

Hedayati-Moghadam, M et al. "The Role of Chemokines in Cardiovascular Diseases and the Therapeutic Effect of Curcumin on CXCL8 and CCL2 as Pathological Chemokines in Atherosclerosis", Adv Exp Med Biol. 2021;1328:155-170.

Hickey, M.A. et al. "Improvement of neuropathology and transcriptional deficits in CAG 140 knock-in mice supports a beneficial effect of dietary curcumin in Huntington's disease", Mol Neurodegener. Apr. 4, 2012;7:12, 16 pages.

Holte, P. ten, et al. "HDAC inhibition in cancer therapy: an increasingly intriguing tale of chemistry, biology and clinical benefit," Cancer. Springer, Berlin, Heidelberg, 2007. 293-331.

Jeengar, M.K. et al. "Emu oil based nano-emulgel for topical delivery of curcumin", Int J Pharm. Jun. 15, 2016;506(1-2):222-236.

Kahkhaie, K.R. et al. "Curcumin: a modulator of inflammatory signaling pathways in the immune system", Inflammopharmacology. Oct. 2019;27(5):885-900.

Kanai, M. "Therapeutic applications of curcumin for patients with pancreatic cancer", World J Gastroenterol. Jul. 28, 2014;20(28):9384-9391.

Kanai, M. et al. "A phase I/II study of gemcitabine-based chemotherapy plus curcumin for patients with gemcitabine-resistant pancreatic cancer", Cancer Chemother Pharmacol. Jul. 2011;68(1):157-164.

Kim, T. et al. "Curcumin activates AMPK and suppresses gluconeogenic gene expression in hepatoma cells", Biochem Biophys Res Commun. Oct. 16, 2009;388(2):377-382.

Lawrence, G.D. "Dietary fats and health: dietary recommendations in the context of scientific evidence", Adv Nutr. May 1, 2013;4(3):294-302.

Lim, G.P. et al. "The curry spice curcumin reduces oxidative damage and amyloid pathology in an Alzheimer transgenic mouse", J Neurosci Nov. 1, 2001;21(21):8370-8377.

Lin, L. et al. "Targeting colon cancer stem cells using a new curcumin analogue, GO-Y030", Br J Cancer. Jul. 12, 2011;105(2):212-220.

Liu, Z. et al."The Inhibitory Effect of Curcumin on Virus-Induced Cytokine Storm and Its Potential Use in the Associated Severe Pneumonia", Front Cell Dev Biol. Jun. 12, 2020;8:479, 10 pages.

Miao, Y. et al. "Curcumin pretreatment attenuates inflammation and mitochondrial dysfunction in experimental stroke: The possible role of Sirt1 signaling", Brain Res Bull Mar. 2016;121:9-15.

Mukherjee, S. et al. "Liposomal TriCurin, A Synergistic Combination of Curcumin, Epicatechin Gallate and Resveratrol, Repolarizes Tumor-Associated Microglia/Macrophages, and Eliminates Glioblastoma (GBM) and GBM Stem Cells", Molecules. Jan. 18, 2018,23(1):201, 21 pages.

Mukherjee, S. et al. "Unique synergistic formulation of curcumin, epicatechin gallate and resveratrol, tricurin, suppresses HPV E6, eliminates HPV+ cancer cells, and inhibits tumor progression", Oncotarget. Mar. 29, 2017;8(37):60904-60916.

Nakmareong, S. et al. "Antioxidant and vascular protective effects of curcumin and tetrahydrocurcumin in rats with L-NAME-induced hypertension", Naunyn Schmiedebergs Arch Pharmacol. May 2011;383(5):519-529.

Nakmareong, S. et al. "Tetrahydrocurcumin alleviates hypertension, aortic stiffening and oxidative stress in rats with nitric oxide deficiency", Hypertens Res. Apr. 2012;35(4):418-425.

Oliviero, F. et al. "Anti-inflammatory effects of polyphenols in arthritis",. J Sci Food Agric. Mar. 2018;98(5):1653-1659.

Purkayastha, S. et al. "Curcumin blocks brain tumor formation", Brain Res. Apr. 17, 2009; 1266:130-138.

Rattis, B.A.C. et al. "Curcumin as a Potential Treatment for COVID-19", Front Pharmacol. May 7, 2021;12:675287, 14 pages.

Rungseesantivanon et al. "Curcumin supplementation could improve diabetes-induced endothelial dysfunction associated with decreased vascular superoxide production and PKC inhibition", BMC Complementary and Alternative Medicine 2010, 10:57; 9 pages.

Satheesh A. et al., "Penetration enhancer accelerated solubilization of curcumin by poly(vinylpyrrolidone)", J. Indian Chem. Soc , vol. 96, Jan. 2019, pp. 14-18.

Sui, Z. et al. "Inhibition of the HIV-1 and HIV-2 proteases by curcumin and curcumin boron complexes", Bioorg Med Chem. Dec. 1993; 1(6):415-422.

Turmeric Curcumin Topical Patches—30 Days Supply—USA Made by Live To Shine,—Amazon.com: Turmeric Curcumin Topical Patches—30 Days Supply USA Made by Live To Shine : Health & Household <https://www.amazon.com/Turmeric-Curcumin-Topical-Patches-Supply/dp/B07G94GHNV/ref=sr_1_5?crid=AICY5YTKFKLJ&keywords=curcumin+patch&qid=1647009345&sprefix=urcumin+patch%2Caps%2C69&sr=8-5>, 1 page.

Turmeric Max Patch—30 Patches—Omni Global Labs, Amazon.com: Turmeric Max Patch—30 Patches : Health & Household <https://www.amazon.com/Turmeric-Max-Topical-Patch-Patches/dp/B07K4W17NC/ref=sr_1_6?crid=AICY5YTKFKLJ&keywords=curcumin+patch&qid=1647009345&sprefix=curcumin+patch%2Caps%2C69&sr=8-6>, 3 pages.

Xu, PH. et al. "The relaxant effect of curcumin on porcine coronary arterial ring segments", Vascul Pharmacol. Jul. 2007;47(1):25-30.

Yang, F. et al. "Curcumin inhibits formation of amyloid beta oligomers and fibrils, binds plaques, and reduces amyloid in vivo", J Biol Chem. Feb. 18, 2005;280(7):5892-5901.

Zendedel, E. et al. "Impact of curcumin on sirtuins: A review", J Cell Biochem. Dec. 2018;119(12):10291-10300.

Tanner & Marks Skin Research and Technology 2008, 14: 249-260.

* cited by examiner

NITRIC OXIDE-RELEASING DEVICE

CROSS-REFERENCE AND RELATED APPLICATION

This patent document claims priority under 35 U.S.C. § 119 (e) to the U.S. Provisional Patent Application 63/238,521 filed on Aug. 30, 2021, the content and teachings of which are incorporated herein by reference in its entirety.

TECHNICAL FIELD

Disclosed herein is a novel device that be can be inserted or applied to a body cavity or surface to release nitric oxide (NO) and methods of treating diseases or disorders using said device.

BACKGROUND

Nitric oxide (NO), also known as nitrosyl radical, is a free radical that is an important signaling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of nitric oxide. The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, hyaline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia.

Clinical translation has proved problematic due to the challenge of delivering sustained therapeutic levels of NO, which is an unstable molecule and thus inherently short lived, and the difficulty in routinely deploying gaseous NO from a gas tank. Current strategies, including NO releasing sprays, do not provide effective sustained delivery.

Thus, there exists a need for a safe and effective production of nitric oxide, which can be used for treatment of various medical diseases and conditions.

SUMMARY

This patent document discloses a device that can release and/or generate nitric oxide (NO) over a surface of a subject or within a body cavity, such as the ears or nose, or other body opening, such as a wound. Nonlimiting example implementations of the device include for treatment or mitigation of the transmission of a communicable disease, development of acute respiratory distress syndrome in Covid-19 patients, sinusitis (including chronic sinusitis), cystic fibrosis, inner and outer ear infections, and diseases or conditions referenced above.

In one aspect, a device for treating a disease or condition is disclosed, comprising:
a nitrite source;
optionally a proton source;
an absorbent reservoir for loading the nitrite source and/or the proton source and configured for being applied to a body cavity of a subject;
wherein the nitrite source and the proton source are selected so that their mixing generates a therapeutically effective amount of nitric oxide.

The proton source may be stored in the device or may be physically separate from the device. In some embodiments, the nitrite source and the proton source are separately stored in the device prior to the device being applied to the body cavity. In some embodiments, the proton source comes from moisture at the site of application of the device. In some embodiments, the proton source is water and/or a gelling agent optionally mixed with a viscosity adjuster.

The nitrite source combines with a suitable proton source to provide immediate and/or extended release of nitric oxide. In some embodiments, the nitrite source may be configured to include both an immediate and an extended-release portion. In some embodiments, the nitrite source comprises an alkali metal nitrite, an alkaline earth metal nitrite, a transition metal nitrite, an ammonium nitrite or any combination thereof. In some embodiments, the nitrite source comprises nitrite loaded nanoparticles.

In some embodiments, one or both of the nitrite source and the proton source are independently admixed with a gelling agent and/or a viscosity adjuster prior to the contact with the proton source. In some embodiments, the gelling agent comprising a material selected from the group consisting of honey, xanthan gum, guar gum, carrageenan gum, locust bean gum, sodium alginate, agar-agar, gelatin, modified starches, cellulose, crosslinked polyacrylic acids, and alkyl-substituted celluloses, wherein the gelling agent optionally further comprises a dilutor for adjusting the viscosity of the gelling agent. In some embodiments, the gelling agent is honey.

The device may include gelling agents and/or viscosity adjusters to modify the release of NO. In some embodiments, the nitrite source and/or the proton source are separately stored in the device from the gelling agent and/or the viscosity adjuster prior to being admixed with the gelling agent and/or the viscosity, and the method comprising admixing the nitrite source and/or the proton source independently with the gelling agent and/or the viscosity adjuster. In some embodiments, one or both of the nitrite source and the proton source are independently admixed with PEG prior to the contact with each other. In some embodiments, the gelling agent and/or the viscosity adjuster and their respective amounts are selected to provide an extended release of a therapeutically effective amount of NO over a period of at least 2 hours, at least 4 hours, at least 8 hours, at least 12 hours, at least 24 hours or at least 48 hours.

The device may further include a thiol source, which can be converted to S-nitrosothiol (SNO) group upon being exposed to NO. In some embodiments, the source of thiol group is thiol-containing molecules. In some embodiments, the thiol source is thiol-containing nanoparticles, which either have the having thiol groups covalently thereto or have thiol-containing molecules loaded in the nanoparticles. In some embodiments, the device includes a source of S-nitrosothiol (SNO) group.

In another aspect provides a method of delivering nitric oxide treating a disease or condition in subject is provided. The method includes placing the device described herein in a body cavity or a surface of the subject in need of such treatment; and allowing the nitrite source and the proton source to react and generate a therapeutically effective amount of nitric oxide.

Nonlimiting examples of the disease or condition treatable with the inventive device include viral or bacterial infections, inflammation, neuropathic pain, sinusitis, cystic fibrosis, bronchiectasis, surgical or trauma induced wounds, vaginal deterioration, and sexual dysfunction. In some embodiments, the device is inserted into the nostril of the subject to treat, for example, chronic sinusitis, neuropathic pain, cystic fibrosis and bronchiectasis. In some embodiments, the device is inserted into the ear of the subject to treat inner or outer ear infections. In some embodiments, the device is applied to the subject prophylactically to prevent or reduce the risk of a disease or health condition.

In another a kit for generating nitric oxide in a bodily cavity or other opening or a surface is provided. The kit includes a nitrite source, optionally a proton source and an absorbent reservoir for loading the nitrite source and optionally the proton source, said absorbent reservoir configured for application to a body cavity or other opening of a subject. The nitrite source is selected so that its mixing with the proton source generates a therapeutically effective amount of nitric oxide.

DETAILED DESCRIPTION

Nitric oxide (NO) has demonstrated promise in the treatment of various diseases and conditions. The device, method of treatment, and kit described in this patent document provide a new exogenous NO therapy, which, unlike therapies of the prior art, is capable of delivering NO directly, specifically and in a sustained manner to bodily tissues in need thereof and could revolutionize the treatment of diseases where increased levels of NO are beneficial.

The novel device disclosed herein allows for water/moisture initiated production and release of NO from a variety of reservoir materials that are suitable as carriers in a suitable body cavity, including for example the nose, nasal sinuses, ears, rectum or vagina, and as coverings for body surfaces, e.g. skin (any of its layers as for example would be the case for a wound) and exposed mucosal surfaces such as the gums. The device allows the release rates and levels of available NO to be adjustable or tunable to the particular therapeutic need, so that they can be matched with the specific indication and site of application.

The device and method disclosed herein can be used to maintain and restore vacular homeostasis, insure and enhance tissue perfusion and oxygen delivery, modulate inflammation, provide very broad spectrum antimicrobial activities against various microbes (e.g. ESKAPE organisms, Fungi including *Candida aurius*), disrupt bacterial and fungal biofilms, accelerate wound healing, simulate mucus production, limit viral replication, maintain normal mucociliary function in the sinuses.

While the following text may reference or exemplify specific embodiments of a device, kit or method relating to NO production, it is not intended to limit the scope of the device, kit or method to such specific embodiments. Various modifications may be made by those skilled in the art, in view of practical and economic considerations. Such modifications may, for example, include the specific source of nitrite and the amount or administration of nitrite source in combination with a gelling agent for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "C1-C18 alkyl" as used herein refers to an alkyl group containing any number (from 1 to 18 inclusive) of carbons in the alkyl group. Nonlimiting examples include methyl, ethyl, propyl, isopropyl, butyl, pentyl, and hexyl.

The term "moisture content" as used herein refers to the amount of water in a composition or formulation. A percentage describing the moisture content is by weight of the water over the total weight of the composition or formulation.

The term "body cavity" includes any opening and surface area within the opening on a subject's body. Nonlimiting examples of body cavity include nose, nasal sinuses, mouth, ears, rectum, vagina, open wound, sore, buccal cavity and mucosal surface (e.g. gum).

The term "applying" in the context of administering the device of this patent document includes inserting, covering, blocking or other suitable manner for using the device on or in the body cavity.

The term "subject" encompasses any animal, but preferably a mammal, e.g., human, non-human primate, a dog, a cat, a horse, a cow, or a rodent. More preferably, the subject is a human.

The term "pharmaceutically acceptable carrier" refers to a chemical compound that facilitates the delivery or incorporation of a compound or therapeutic agent into cells or tissues.

The term "therapeutically effective amount" or "effective amount" refers to an amount of an agent, compound or composition effective to prevent, alleviate or ameliorate symptoms of disease, prolong the survival of the subject being treated, or reach a desirable/acceptable medical or sanitary condition. Determination of a therapeutically effective amount or effective amount is well within the capability of those skilled in the art, especially in light of the detailed disclosure provided herein.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. Treatment for prophylactic purpose is to be construed as any mode of treatment that is used to prevent progression of the disease or is used for precautionary purpose for persons at risk of developing the condition.

I. Device

An aspect of this document provides a device configured to be applied to a body cavity of a subject for treating a disease or condition requiring application of NO. The device includes: a nitrite source; optionally a proton source (included in the device or separate from the device; and a reservoir for loading the nitrite source and the proton source.

The nitrite source and/or the proton source are selected so that their mixing generates a therapeutically effective amount of nitric oxide.

The reservoir is preferably made from a material capable of storing the nitrite source and/or the proton source, or absorbing liquid containing the nitrite source and/or the proton source and is in a shape suitable for being applied to a body cavity of a subject. For example, the reservoir can be made from a material which absorbs liquid through capillary action. Alternatively, the material may be hydrophilic or hygroscopic or coated with a hydrophilic or hygroscopic layer that exhibits affinity for aqueous solution, especially water moisture for example from the site or body cavity where the reservoir is placed. A reservoir with absorbant characteristics can be made from natural or synthetic materials, which include for example polyester, polyurethane, and vegetal cellulose.

The reservoir can also be a container with one or more structural sub-units for storing individual components (e.g. nitrite source, proton source, thiol source, etc) and include one or more apertures for in-flowing of proton source (e.g. water) and/or releasing of NO generated in the container. For example, a reservoir can enclose therein nitrite source and optionally thiol source. After adding water to the reservoir through an aperture of the reservoir, NO will be subsequently released. Of course, the reservoir can also include a frangile pouch or capsule for storing a proton source. The breaking of the pouch or capsule will then lead to the mixing of the proton source with the nitrite source.

Nonlimiting examples of the reservoir include a sponge, a tube, an implant or a patch and can be in any suitable form or shape to be applied to a body cavity. In some embodiments after application of the reservoir to the body cavity, the expansion of the reservoir is less than 20%, less than 10%, less than 5%, or less than 1% in volume. The reservoir can be single use or configured for multiple use of repeated loading of the e.g., nitrite source and the proton source. In some embodiments, the reservoir includes a porous substrate for absorbing the nitrite source and/or the proton source. In some embodiments, the reservoir includes two or more chambers which separately store the nitrite source and the proton source. The barriers between the chambers can be broken under pressure. In some embodiments, the nitrite source is enclosed in a pouch or capsule, which is made from materials that break down upon contact with water.

The reservoir can be made into a desirable size or shape (e.g., circular, cylindrical, cone, planar, and other symmetrical or asymmetrical shape) for inserting or applying to the body cavity, and may include an applicator or applicator portion.

The nitrite source and the proton source can be mixed together or physically separate from each other prior to being applied to the subject. Preferably, the nitrite source and the proton source are separated from each other until or shortly before the device is applied to the subject. In some embodiments, the device includes a proton source. In some embodiments, the device does not include a proton source.

The proton source can be from moisture at the location where the device is applied, from an external source outside the subject, or a combination of both. In some embodiments, the proton source is water or an aqueous solution (buffered, unbuffered, or acidified) or a molecule containing a releasable proton (e.g., N-acetyl cysteine (NAC), an alcohol such as ethanol or propanol, a carboxylic acid, an optionally substituted phenol). In some embodiments, the proton source consists essentially of an organic molecule containing a releasable proton.

In some embodiments, the proton source is a gelling agent and/or viscosity adjuster optionally admixed with water in a predetermined ratio. The gelling agent or viscosity adjuster has higher viscosity than water and serves to enhance the stability of the nitrite source and control the rate of proton release. For instance, by sequestering the nitrite source within the gelling agent, the nitrite remains stable or dormant until exposed to a proton source. The gelling agent or nitrite viscosity adjuster has a viscosity ranging from about 50 to about 25,000, from about 80 to about 20,000, or from about 5000 to about 15,000 centipoise. In some embodiments, the viscosity of the gelling agent or embodiments viscosity adjuster is at least 80, at least 90, at least 100, at least 500, at least 1000, at least 2000, at least 5000, at least 10,000, or at least 15,000 centipoise.

The low amount of moisture in the gelling agent is generally insufficient to initiate a fast NO production. When the nitrite source is in contact with water source (with or without buffer) or a proton source, nitrous acid is formed and then decomposes to release dinitrogen trioxide ($N_2O_3$), which can further produce NO. The production is slow or inhibited when the nitrite source is dry or when the gelling agent minimizes the contact with water. However, when water or a proton source is injected into the gelling agent in contact with the nitrite source, $N_2O_3$ and NO gas start to form. By controlling the viscosity of the gelling agent and the amount of water or the acid source, the rate and length of NO release can be controlled. Therefore, at least in some cases, the gelling agent serves to insulate the nitrite source from moisture prior to the intended NO formation and mediate at adjusted viscosity if necessary the contact with water during NO formation. In some embodiments, the moisture content in the gelling agent prior to the intended NO formation and release is less than about 15%, includes less than 10%, less than 5%, less than 2% or substantially free from water.

Nonlimiting examples of the gelling agent include honey, xanthan gum, guar gum, carrageenan gum, locust bean gum, sodium alginate, agar-agar, gelatin, modified starches, methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, co-polymers of carboxyvinyl polymers, co-polymer of acrylates, co-polymers of oxyethylene and oxypropylene and mixtures thereof. In some embodiments, the gelling agent is a reducing sugar, which can be one or more monosaccharides (e.g., galactose, glucose and fructose), disaccharides (lactose and maltose), oligosaccharides, or polysaccharides. In some embodiments, the gelling agent is honey. The honey can be raw or processed. Honey is generally hygroscopic and weakly acidic. A preferred type of honey is medicinal honey or Manuka honey, which is widely known to exhibit antibiotic activities. Manuka honey, made from the nectar of the Manuka tree (tea tree), has exceptional phytochemical-derived, antimicrobial properties, e.g., antibacterial, antifungal, and/or anti-viral properties. Manuka honey contains methylglyoxal, and that methylglyoxal gives rise to the antimicrobial properties of Manuka honey. Methylglyoxal has more advantageous properties than the hydrogen peroxide produced in all raw honey from glucose oxidase, which comes from bees during honey production. In particular, Manuka honey also contains methylglyoxal, which may contribute to the reduction of the nitrite to NO.

In some embodiments, the gelling agent insulating or entrapping the nitrite source does not contain water or is substantially from water. In some embodiments, the gelling agent may pull in water from the environment or the cavity or surface of the subject being administered. In some embodiments of initiating NO formation, the gelling agent entrapping the nitrite source is admixed with water in a ratio by weight between the gelling agent and water ranging from about 1000:1 to 1:100, from about 100:1 to 1:100, from about 50:1 to 1:50, from about 10:1 to 1:10, or from about 5:1 to 1:5. Nonlimiting examples of the ratio between the gelling agent and water include about 1000:1, about 100:1, about 50:1, about 10:1, about 8:1, about 6:1, about 4:1, about 2:1, about 1:1, about 1:2, about 1:4, about 1:4, about 1:6, about 1:8, and about 1:10.

In some embodiments, the proton source needed to initiate NO and SNO formation by the nitrite is medicinal honey with or without added water, N-acetyl cysteine, or acidified solutions containing water with or without PEG Controlled release of NO can also be achieved using a combination of water and/or gelling agent with a viscosity adjuster. Prior to initiation of NO formation, a visocosity adjuster can be admixed with the gelling agent and/or the water source. The viscosity adjusters for the gelling agent and the water source can be the same or different. Nonlimiting examples of the viscosity adjuster include polypropylene glycol, polyethylene glycol, glycerol, fatty acid, petroleum jelly, K-Y jelly, other hydrophilic molecules, and any combination thereof. Nonlimiting examples of fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, myristic acid and any combinations thereof. Mid-sized fatty acids such myristic acid and/or other fatty acids of comparable size/molecular weight are particularly useful. In some embodiments, the viscosity adjuster does not contain fatty acid or contains only a trace or an insignificant amount of fatty acid. In some embodiments, the fatty acid is myristic acid. In some embodiments, the viscosity adjuster is polyethylene glycol (PEG) optionally in combination with a fatty acid. The molecular weight of the viscosity adjuster or PEG may range from about 100,000 to 800,000, from about 100,000 to 400,000, from about 200,000 to 400,000, from about 100 to 20,000, from about 200 to 10,000, from about 200 to 5,000, from about 200 to 1,000, from about 200 to 500 daltons. Further examples include about 100, about 200, about 300, about 400, about 500, about 600, about 800, and about 1000 daltons.

When mixed with a proton source or water, the viscosity adjuster increases the viscosity of the mixture and thus controls the rate of NO generation and release. The ratio by weight between water and the viscosity adjuster may range from about 100:1 to 1:100, from about 50:1 to 1:50, from about 10:1 to 1:10, or from about 5:1 to 1:5, with or without additional gelling agent. Nonlimiting examples of the ratio between water and the viscosity adjuster include about 10:1, about 8:1, about 6:1, about 4:1, about 2:1, about 1:1, about 1:2, about 1:4, about 1:4, about 1:6, about 1:8, and about 1:10. Likewise in some embodiments, a gelling agent can be admixed with a proton source or water, and the nitrite source can be with or without an insulating gelling agent. The ratio by weight between the proton source or water and the gelling agent may range from about 100:1 to 1:100, from about 50:1 to 1:50, from about 10:1 to 1:10, or from about 5:1 to 1:5, with or without an additional viscosity adjuster.

In some embodiments, the viscosity adjuster includes a combination of small and large polyalkylene glycols, which have a molecular weight (MW) difference ranging from 500 to 5000, from 1000 to 3000, from 1000 to 2000, or from 1500 to 2000 Daltons. By adjusting the ratio between the two or more polyalkylene glycols, viscosity of the resulting mixture and rate/extent of NO penetration and uptake by the circulation can be controlled. For instance, the combination may include one or both of PEG and PPG each having a MW ranging from 100 to 2000, from 200 to 2000, from 400 to 1000, or from 500 to 800 Daltons. The combination may also include one or both of PEG and PPG each having a higher MW ranging from 800 to 5000, from 1000 to 3000, or from 1000 to 2000 Daltons. In further exemplary embodiments, one of polyalkylene glycols has MW of 100, 200, 400, 600, or 800, and another of the polyalkylene glycols has MW of 1000, 1500, 2000, 2500, or 3000. In some embodiments, the combination includes a PEG of 400 and a PEG of 2000 Daltons. In some embodiments, the ratio between the low MW polyalkylene glycol and the high MW polyalkylene glycol ranges from about 10:1 to about 1:10, from about 5:1 to about 1:5, from about 2:1 to about 1:2 by weight. Further exemplary ratios between the low MW polyalkylene glycol (e.g. PEG and/or PPG) and the high MW polyalkylene glycol (e.g. PEG and/or PPG) include 10:1, 8:1, 6:1, 4:1, 2:1, 1:1, 1:2, 1:4, 1:6, 1:8 and 1:10.

The viscosity adjuster (e.g., PEG) and/or the gelling agent can also provide a molecular cage surrounding NO releasing molecules and particles and as a result can significantly slow the release of NO as does the enhanced viscosity of these two materials. In some embodiments, the gelling agent is admixed with the viscosity adjuster to fine tune the viscosity of the mixture in order to achieve a desirable rate of NO release. The ratio between the gelling agent and the viscosity adjuster can be adjusted depending on the intended use. In some embodiments, ratio by weight between the gelling agent and the viscosity adjuster ranges from about 50:1 to about 1:10, from about 10:1 to about 1:10, from about 5:1 to about 1:5, from about 2:1 to about 1:5, from about 1:1 to about 1:5, from about 1:1 to about 1:2, or from about 1:1 to about 1:3. Nonlimiting examples of the ratio between the gelling agent and the viscosity adjuster include about 10:1, about 8:1, about 6:1, about 4:1, about 2:1, about 1:1, about 1:2, about 1:4, about 1:4, about 1:6, about 1:8, and about 1:10.

In some embodiments, the ratio by weight between the viscosity adjuster (for insulating/entrapping the nitrite source) and the nitrite source ranges from 5:1 to about 5000:1, from about 50:1 to about 5000:1, from about 50:1 to about 1000:1, from about 100:1 to about 1000:1, from about 200:1 to about 1000:1, from about 200:1 to about 500:1 or from about 200:1 to about 1000:1. Nonlimiting examples of the ratio between the viscosity adjuster (for entrapping the nitrite source) and the nitrite source include about 10:1, about 20:1, about 50:1, about 80:1, about 100:1, about 200:1, about 500:1, about 200:1, about 500:1, about 1000:1, about 2000:1. In some embodiments, a viscosity adjuster with a suitable viscosity replaces the gelling agent for entrapping or insulating the nitrite source and the device is free from a gelling agent. In some embodiments, the nitrite source is substantially distributed or entrapped within the viscosity adjuster.

In some embodiments, low molecular weight PEG (e.g. PEG200 and PEG400) is combined with the gelling agent (e.g. honey) to reduce viscosity. In some embodiments, the PEG can serve to dissolve the nitrite to a concentration of about 100 mM, about 200 mM, about 300 mM, about 400 mM, about 500 mM, or about 600 mM. In some embodiments, the nitrite is saturated in PEG.

The nitrite source can be synthetic, natural, or a combination of synthetic and natural sources. Nonlimiting examples of the nitrite source include alkali metal nitrite, an alkaline earth metal nitrite, a transition metal nitrite and an ammonium nitrite. In some embodiments, the nitrite source is potassium nitrite, sodium nitrite, rubidium nitrite, strontium nitrite, barium nitrite, calcium nitrite, copper nitrite, zinc nitrite, or mixtures thereof. Nitrite can also be obtained from a natural source such as extracts of lettuce and spinach. In some embodiments, the amount of the nitrite source (calculated by the weight of the nitrite ($NO_2^-$) group) in the device or a unit dosage ranges from about 0.0001 mg to about 5000 mg, from about 0.001 mg to about 5000 mg, from about 0.01 mg to about 5000 mg, from about 0.1 mg to about 5000 mg, from about 1 mg to about 1000 mg, from about 10 mg to about 500 mg, or from about 10 mg to about 100 mg. Nonlimiting examples of the amount of the nitrite group in a dosage unit or in a device include about 0.0001 mg, about 0.0002 mg, about 0.0004 mg, about 0.0006 mg, about 0.0008 mg, about 0.001 mg, about 0.002 mg, about 0.004 mg, about 0.006 mg, about 0.008 mg, about 0.01 mg, about 0.02 mg, about 0.04 mg, about 0.06 mg, about 0.08 mg, about 0.1 mg, about 0.2 mg, about 0.4 mg, about 0.06 mg, about 0.08 mg, about 1 mg, about 2 mg, about 5 mg, about 10 mg, about 20 mg, about 30 mg, about 40 mg, about 50 mg, about 60 mg, about 80 mg, about 100 mg, about 200 mg, about 300 mg, about 400 mg, about 500 mg, about 600 mg, about 800 mg, about 1 g, about 2 g, about 5 g, and about 10 g.

The cage effect arising from high viscosity, relatively rigid matrices, the internal mileu of the nano/micro particles can be used to slow production and release of NO from both nitrite and S-nitrosothiols. In some embodiments, the nitrite is loaded in nanoparticles or microparticles, which are stable in the gelling agent (e.g. honey). Only when the water content increases will the nitrite be converted to NO and be released. The preparation of nitrite-loaded particles has been reported in literature, including U.S. Pat. No. 8,333,997, U.S. Patent Application No. 20160175348, and Methods Mol Biol. 2010; 704:187-95. PubMed PMID: 21161638. The entire disclosures of all these references are incorporated herein by reference. The preparation of nitrite loaded nanoparticles/microparticles under high pH conditions can prevent the acid initiated formation of NO from the nitrite. After the nitrite loaded particles are mixed with gelling agent (e.g. honey), they will remain stable/dormant until the gelling agent pulls in sufficient water to provide sufficient mobile protons to facilitate NO and N2O3 production from within the particles. Having the nitrite sequestered in the particles thus provides a more concentrated and/or more stable (with respect to generating NO prematurely) component compared to free nitrite exposed to environment. The nitrite loaded particles therefore represent an approach for incorporating high concentrations of nitrite into the reservoir, eg. sponges, inserts etc., without triggering spontaneous NO and S—NO production in the absence of moisture/water.

In some embodiments, the device does not contain nano or micro particles. Preferably, the nitrite source is evenly or uniformly distributed in the reservoir as opposed to, for example, being stored, attached or encapsulated to individual particles which are then loaded to the reservoir.

The amount of water source or proton source can be controlled to adjust the rate of NO release. In some embodiments, the amount of water or proton source ranges from about 0.2 to about 10 equivalents of the nitrite source, from about 0.5 to about 10 equivalent of the nitrite source, from about 0.2 to about 5 equivalent of the nitrite source, from about 0.5 to about 10 equivalent of the nitrite source from about 1 to about 5 equivalent of the nitrite source, from about 0.5 to about 2 equivalent of the nitrite source, or from about 0.5 to about 1.5 equivalent of the nitrite source.

The ratio between the weight of the gelling agent and the weight of nitrite source depends on various factors including the specific agents and the intended applications. In some embodiments, the ratio by weight between the gelling agent and the nitrite source ranges from about 1:5 to about 5:1, from about 1:2 to about 2:1, from about 1:1 to about 5:1, from about 5:1 to about 5000:1, from about 50:1 to about 5000:1, from about 50:1 to about 1000:1, from about 100:1 to about 1000:1, from about 200:1 to about 1000:1, from about 200:1 to about 500:1 or from about 200:1 to about 1000:1. Nonlimiting examples of the ratio between the gelling agent and the nitrite source include about 1:2, about 1:1, about 2:1, about 5:1, about 10:1, about 20:1, about 50:1, about 80:1, about 100:1, about 200:1, about 500:1, about 200:1, about 500:1, about 1000:1, about 2000:1. In some embodiments, the nitrite source is substantially distributed or entrapped within the gelling agent. An extended or sustained release of NO is mediated through the gelling agent which controls the exposure of the nitrite source to water or physiological environment and the release of in situ formed gas.

The device may further contain a thiol source, which can be converted to S-nitrosothiol through a nitrite-based reaction such as a reaction with dinitrogen trioxide derived from the nitrite reaction with water. Formation of S-nitrosothiols is a mechanism for creating sustained NO release and thus extending the biological activity of nitrite derived NO. The thiol source may include nanoparticles or microparticles having thiol groups covalently bonded to the backbone structure of the particle or releasable molecules (e.g., Glutathione, NAC, N-acetylpenicillamine, human serum albumin containing the thiol groups) enclosed within or bonded to the nanoparticles. Various preparation methods of thio-containing nanoparticles have been reported in literature. For example, nanoparticle forming materials can be doped with molecules containing a thiol group so that the thiol containing molecule gets encorporated into the polymeric make up of the particle. Further examples include thiol containing silanes resulting in a thiol doped silica matrix. Additional synthesis procedures relating to thiol-containing particles are disclosed in the following literature: J Colloid Interface Sci. 2015; 459:115-22. Epub 2015 Aug. 16. doi: 10.1016/j.jcis.2015.08.011. PubMed PMID: 26275504; ACS Appl Mater Interfaces. 2019; 11(13):12216-23. Epub 2019 Mar. 20. doi: 10.1021/acsami.8b19236. PubMed PMID: 30888145; PMCID: PMC6773253; J Mater Chem B. 2016; 4(11):2051-8. Epub 2016 Mar. 21. doi: 10.1039/c5tb02551f. PubMed PMID: 32263082; Int Forum Allergy Rhinol. 2018; 8(10):1190-8. Epub 2018 Jul. 26. doi: 10.1002/alr.22185. PubMed PMID: 30044542. The entire disclosure of these publications are hereby incorporated by reference.

The thiol source can also include thiol-containing molecules such as glutathione or NAC. These molecules can also be modified to form the corresponding ester or amide (e.g., C1-C18 alkyl esters of NAC as well as amides of NAC) and become more lipophilic than NAC. By varying the carbon chain of these molecules the properties of the molecule can be tailored. Nonlimiting examples for the thiol source include molecules containing the thiol group (e.g., Glutathione, NAC, N-acetylpenicillaminem, cysteine, and their derivatives) with or without nanoparticles or microparticles, and also include for example thiol containing hydrogel-based nanoparticles or microparticles and thiol coated paramagnetic and ferromagnetic nanoparticles or microparticles. For instance, thiol containing molecules can be included in honey or honey-PEG mixtures as a source of thiols for the production of S-nitrosothiols derived from the water initiated nitrite reaction in the nitrite loaded particles.

The mole ratio between the nitrite in the nitrie source and the thiol in the thiol source ranges for example from about 50:1 to about 1:10, from about 5:1 to about 1:5, from about 2:1 to about 1:5, from about 1:1 to about 1:5, from about 1:1 to about 1:2, or from about 1:1 to about 1:3. By controlling the mole ratio, the rate of NO release can be modified and and a sustained release phase can be achieved with desirable rate of NO generation. In some embodiments, the thiol source is admixed with the nitrite source prior to the NO generation.

The device may further contain a source of S-nitrosothiol (SNO) groups. A sustained release of NO at higher amount can be achieved as a result. In some embodiments, the source of the S-nitrosothiol groups is nanoparticles or microparticles covalently attached to the S-nitrosothiol groups or S-nitrosothiol group containing molecules. The particles can be lipophilic, hydrophilic, or a combination of them depending on the specific applications. The SNO source may be admixed with the nitrite source or loaded into separate container unit (e.g. pouch) of the device.

In some embodiments, the source of S-nitrosothiol groups is releasable molecules containing S-nitrosothiol groups attached to or enclosed by nanoparticles or microparticles. Nonlimiting examples of the such releasable molecules are selected from the group consisting of S-nitroso-Glutathione (GSNO), S-nitroso-N-acetylcysteine (SNAC or NACSNO), S-Nitroso-N-acetylpenicillamine (SNAP), S-nitroso-human serum albumin (SNO-HSA) or any combination thereof.

Various procedures can be employed for the preparation of SNO containing nanoparticles including for example NACSNO, GSNO, SNO-NP/MP. Exemplary procedures include those reported in the literature, including Nanomedicine. 2015; 11(2):283-91. doi: 10.1016/j.nano.2014.09.017. PubMed PMID: 25461287; Journal of drugs in dermatology: JDD. 2015; 14(7):726-32. PubMed PMID: 26151790; Nitric Oxide. 2012; 27(3):150-60. doi: 10.1016/j.niox.2012.06.003. PubMed PMID: 22705913; PMCID: 4156139; and Int Forum Allergy Rhinol. 2020; 10(2):223-32. doi: 10.1002/alr.22472. PubMed PMID: 31834677. Additional reports on the preparation of SNO containing nanoparticles are available in U.S. Patent Application No. 20160175348. The entire disclosures of all of the references cited in this paragraph are hereby incorporated by reference.

The mole ratio between the nitrite (in the nitrite source) and S-nitrosothiol (in the SNO-containing molecule/particle) or between the nitrite and the thiol (in the thiol-containing particle or molecule) ranges for example from about 10:1 to about 1:10, from about 5:1 to about 1:5, from about 2:1 to about 1:5, from about 1:1 to about 1:5, from about 1:1 to about 1:2, or from about 1:1 to about 1:3. By controlling the mole ratio, the relative amplitudes for a burst phase of NO release can be controlled and a sustained release phase can be achieved with desirable rate of NO generation.

In any embodiment disclosed herein, the nanoparticle or microparticle may have a particle size or average diameter ranging from about 10 to about 2000 nm, from about 10 to about 1000 nm, from about 50 to about 1000 nm, from about 50 to about 500 nm, from about 100 to about 800 nm, from about 100 to about 600 nm, from about 100 to about 500 nm, from about 400 to about 600 nm, from about 200 to about 500 nm, or from about 20 to about 400 nm.

There may also be included for each of the above-described components (e.g., proton source, nitrite source, thiol source and SNO source) one or more physiologically acceptable carriers, diluents, excipients, including for example, smoothing agents, suspension agents, film forming substances, and coating assistants, or a combination thereof. For instance, the proton source may include other excipients such as aqueous buffers, petroleum jelly and K-Y jelly for specific indications.

Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, fragrances, flavoring agents, and the like may be provided in the components described herein.

The above-mentioned components (e.g., proton source, nitrite source, thiol source and SNO source), individually or in combination, may be in the form of, for example, a suspension, a solution, a foam, a spray, an ointment, a cream, or an aerosol in the device for administration to a subject in need. The components may also be prepared or packaged into a discrete solid dose unit including, but not limited to, a tablet, a hard or soft capsule, a pouch, a cachet, a troche, an ampule, or a lozenge, each containing a predetermined amount of, for example, one, two, or more of the nitrite source, the gelling agent, the water, the water-PEG mixture, the water-gelling agent mixture with or without PEG, and the thiol source. After being loaded into the device, the coating of these dose unit starts to disintegrate upon contact with water or physiological environment in a subject and allows the NO production to take place. Alternatively, the dose unit can be made from frangible material, which ruptures or is crushed under force to expose the contents therein for generation of NO. Two or more of the nitrite source, the gelling agent, the viscosity adjuster, the proton source and the optional thiol source can be packaged into the same or different frangible or dissolvable dose unit container for loading into the reservoir. For example, the nitrite source and the optional thiol source can be in the same dose unit container with or without the gelling agent and/or the viscosity adjuster. The proton source can be directly loaded into the reservoir or packaged into a frangible or dissolvable dose unit container separate from the nitrite source or optional thiol dose unit container. An alternative to using two separate dose unit containers is using a single container having two separate chambers enclosing different components. For example, one chamber may contain a nitrite source and/or thiol source and another chamber may contain the proton source, e.g. water or gelling agent and/or viscosity adjuster optionally admixed with water in a predetermined ratio.

For example, a nitrite source, a proton source, and optionally a thiol source and other components can be mixed as a viscosity solution, a suspension, a gel, an emulsion, a spray or any suitable form for loading into the reservoir such as a sponge, an insert, or a pad having the property of being able to rapidly absorb the NO releasing combination mixture. The loaded reservoir can then be either inserted or placed into/onto the targeted site (e.g. nasal sinus, ear canal, wound).

Alternatively, a reservoir such as a sponge or an insert can be embedded/loaded with a frangible pouch or a dissolvable capsule containing a dry mixture of a nitrite source (e.g nitrite salt or nitrite loaded particles) and a thiol containing molecule or nanoparticle. NO generation can be initiated after the frangible pouch is crushed or when the dissolvable capsule dissolves in the presence of a suitable proton source (e.g. water, water+PEG400, water plus medicinal honey, and medicinal honey plus PEG) absorbed to the sponge or insert.

In some embodiments, one, two, three or more components (e.g., proton source, nitrite source, thiol source and SNO source) of the device are enclosed, partially or completely, within the reservoir in order to minimize the leaking of the residues from the NO formation reaction to the application site. Each of the components may further be enclosed in a frangible pouch or capsule. For instance, a frangible or dissolveable capsule enclosing the nitrite source and/or the thiol-containing nanoparticles and an additional capsule enclosing the proton source can be further enclosed within the reservoir (e.g. sponge). After the content of the capsules are released to form NO, the solid materials are trapped in the reservoir to avoid contamination of application site.

The viscosity of the gelling agent/viscosity adjuster, the use of particles loaded with nitrite source or thiol source, the nature of the reservoir (e.g. sponge matrix) can contribute to the creating of a sustained release profile for NO that can be manipulated and tuned to the requirements of specific indications. For example, one, two, three or more of the following can be used for controlled NO release: viscosity enhancer and/or gelling agent mixed with or enclosing a nitrite source loaded in the reservoir or enclosed in a frangible or dissolvable dose unit container; nanoparticles loaded with nitrite source; nanoparticles loaded with thiol source; a proton source comprising a mixture of the gelling agent, optionally a predetermined or very limited or no amount of water and an optional viscosity enhancer. The nanoparticles can be directly loaded in the reservoir or enclosed in a frangible or dissolvable dose unit container.

In some instances, the water adsorbed from the application, insertion or localization site (e.g. the nasal sinus, the skin, a wound, the ear canal) may be sufficient to activate the process without the need to apply an aqueous solvent prior to application or insertion. A combined strategy entails loading a gelling agent or viscosity adjuster (e.g. PEG) to the reservoir containing the frangible pouch or dissolvable container which will create a higher viscosity internal environment which will slow the release of NO when water is taken up after application or insertion. The gelling agent or viscosity adjuster can be mixed with the nitrite source and/or thiol source in the container or is applied to the outside of the container as long as it forms a barrier to slow down the rate of NO generation and/or release. Variations on this strategy include using nano/micro particles either with thiols covalently bound in the particle matrix or particles in which thiol containing molecules (e.g. NAC) are encapsulated in a nano/micro particle. The use of the nano/micro particles both for nitrite and the thiols will greatly slow down and extend the release profile for NO.

In an example of rapid onset initiation of the NO generation, a dry mix of a thiol-containing small molecule (e.g. N-acetyly cysteine, glutathione, penacillamine, cysteine) and either a nitrite salt or a nitrite loaded nano/micro particle to which is added, either by direct mixing in a vessel or by breaking frangible pouches, a proton source including:

1. water with or with out buffering to be added to and mixed with the dry materials at the time of desired activation of the NO releasing sponge, insert, pad etc.
2. a solution comprising a small molecular weight PEG (e.g. PEG200, PEG400) and a variable amount of water (buffered or not buffered) where the water enhances solubility of both the nitrite and the thiol-containing molecules and the PEG by increasing and tuning viscosity, slows and extends NO release. The solvent and the dry materials are to be combined and mixed at the time of the desired activation
3. a solution comprising medicinal honey (e.g. derived from manuka honey) and added water where the honey controls viscosity, provides therapeutic potential for wounds and infection and supplies protons to initiate NO formation from nitrite.

In an example of slow moisture initiated NO generation, the process is triggered by the pulling in of water by the hygroscopic component of highly viscous and slightly acidic hygroscopic liquid such as medicinal honey loaded with/mixed with one or any combination of:

1. a nitrite salt and N-acetyl cysteine (NAC) (or other suitable thiol containing molecule).
2. nitrite loaded nano/micro particles and N-acetyl cysteine (NAC) (or other suitable thiol containing molecule).
3. nitrite salt or nitrite loaded nano/micro particles with either thiol modified nano/micro particles (thiol groups chemically incorporated into the polymeric make up of the particles) or nano/micro particles loaded with NAC or other suitable thiol containing small molecules.

In an example of slow moisture initiated NO generation triggered by the pulling in of water by the hygroscopic component, a solvent based on small molecular weight liquid polyethylene glycol (e.g. PEG200 and PEG400) into which one can have the option of a dissolved viscogenic agent such myristic acid that can allow for the facile tuning and temperature sensitivity of the overall viscosity of the solvent. The solvent can be used to form mixtures/slurries with the following:

1. a nitrite salt and N-acetyl cysteine (NAC) (or other suitable thiol containing molecule).
2. nitrite loaded nano/micro particles and N-acetyl cysteine (NAC) (or other suitable thiol containing molecule).
3. nitrite salt or nitrite loaded nano/micro particles with either thiol modified nano/micro particles (thiol groups chemically incorporated into the polymeric make up of the particles) or nano/micro particles loaded with NAS or other suitable thiol containing small molecules.

A combination of fast and slow profiles within the same reservoir can be achieved by having a combination of immediate release portion (e.g. containing free and uninhibited nitrite source) and extended release portion (containing any of the above described controlled release strategies). For instance, a mixture of both free nitrite/thiols and nano/micro particle encapsulated nitrite/thiols provides a dual release profile: rapid release component (particle independent reactions) and the slower particle controlled release component. Both fast and slow profiles can be further adjusted by the choice of application of a viscogenic solvents (e.g. PEG400) prior to insertion. Likewise, a combination of a free nitrite portion (nitrite salt or nitrite loaded nanoparticles unentraped by gelling agent or viscosity enhancer) and an entraped nitrite portion of nitrite salt or nitrite loaded particles will provide an initial burst of NO followed by sustained release. Additional examples include using multiple embedded frangible or dissolveable containers (e.g. pouches, capsules) where one container contains the dry NO generating agents (nitrite source and optional thiol source) free from gelling agent or viscosity enhancer and another container has a high viscosity agent (e.g. medicinal honey, PEG, PEG+myristic acid) enclosing the nitrie source and optional thiol source. Another variation is using a container that has two separate chambers whose content get mixed when the frangible pouch gets crushed or when the capsule dissolves in the presence of water. In some embodiments, the nitrite in the immediate release portion and the nitrite in the extended release portion have a ratio by mole ranging from about 1:30 to about 30:1, from about 1:20 to about 20:1, from about 1:20 to about 10:1, from about 1:20 to about 1:1, from about 1:20 to about 1:10, from about 1:20 to about 1:5. Nonlimiting examples of the ratio between the nitrite in the immediate release portion and the nitrite in the extended release portion include about 1:25, about 1:15, about 1:10, about 1:5, about 1:1, and about 5:1.

The device disclosed herein can be in any form for application. In some embodiments, the reservoir is a nasal sponge, pad, insert, or other suitable structure, to which is added, prior to clinical insertion, an appropriate aliquote of a solution/mixture/emulsion/liquid (containing one or more components of nitrite source, proton source, thiol source, and SNO source) that will release in a sustained manner, therapeutically relevant levels of nitric oxide upon uptake of moisture by the composite material (e.g. sponge with absorbed NO generating emulsion. The reservoir should have the property of fully absorbing the applied nitric oxide generating solution/mixture/emulsion/liquid prior to clinical insertion or application (skin or mucosal surface in the mouth). In some embodiments, the reservoir is a sponge or any other appropriate insert, into the core of which is injected NO generation materials (containing one or more components of nitrite source, proton source, thiol source, and SNO source) that will generate sustained levels of therapeutically relevant levels of nitric oxide upon uptake of moisture by the sponge material, the injected formulation or a combination of both. In some embodiments, the reservoir is a sponge or any other appropriate insert with an engineered hollow central cavity into which is inserted one or more frangible pouches filled with NO generation materials that upon physical rupture start to generate nitric oxide either upon uptake of moisture or through the combination of released agents. The single frangible pouch could have dual or multiple chambers each containing different components which when combined upon rupture of the pouch can initiate NO production either with or without the addition of moisture/water. In some embodiments, the reservoir is a sponge, an insert or any other appropriate form into which is embedded a capsule(s) that dissolves upon exposure to water. The capsule contains nitrite (salt of particle encapsulated) and a source of thiols (free or particle associated).

Temperature dependent viscosity can be used to control stability during storage and NO release. Enhancing the viscosity by lowering the temperature can be used to slow or stop NO production and release during storage. For example, honey, PEG400-myristic acid combination and to a lesser extent PEG400 alone show dramatic enhancement of viscosity upon refrigeration or freezing. Lower temperature also allows for extended storage of NO, for example after formation of an S-nitrosothiol group from thiol group and NO. In some embodiments, the temperature of the device or one or more or all components (e.g., proton source, nitrite source, thiol source and SNO source) prior to application may range from about −50° C. to about 50° C., from about −30° C. to about 20° C., from about −20° C. to about 10° C., from about −20° C. to about 0° C., from about −20° C. to about −10° C., from about −10° C. to about 10° C., or from about −10° C. to about 0° C. Non-limiting examples of the temperature prior to application include about −30° C., −20° C., −15° C., −10° C., −5° C., 0° C., 5° C. and 10° C.

Additional pharmaceutically acceptable carriers can be added to the components to facilitate the manufacturing or storage of the device and the delivery of NO to the subject in need. For instance, when the device is configured for topical application over an open wound, an oil medium such as peanut oil, liquid paraffin, or olive oil can be incorporated into one or more the above descried components. The device may also include a medium or a layer that facilitate loading of the components and/or limit or even prevent access of the chemicals or particles to skin but allow for the production of diffusible NO to access the target area. The device may further contain various additional ingredients including, but not limited to, antioxidants, antibiotics, antifungal agents, and/or preservatives.

In some embodiments, the device components (e.g. nitrite source, proton source, gelling agent, viscosity modifier, etc.) are configured and their amounts are selected so that the device provides an extended release of NO, to the cavity or surface of the subject, at a level of at least 0.2 ppm, at least 0.5 ppm, at least 1 ppm, at least 5 ppm, at least 10 ppm, at least 15 ppm, at least 20 ppm, at least 40 ppm, at least 60 ppm, at least 80 ppm, at least 100 ppm, at least 150 ppm, at least 200 ppm, at least 250 ppm, at least 300 ppm, at least 400 ppm, at least 500 ppm, at least 1,000 ppm, at least 2,000 ppm, at least 5,000 ppm, at least 10,000 ppm, at least 50,000 ppm, at least 100,000 ppm, at least 500,000 ppm, or at least 1,000,000 ppm over a period of at least 10 minutes, at least 30 minutes, at least 1 hour, at least 2 hours, at least 4 hours, at least 8 hours, at least 12 hours, at least 16 hours, at least 24 hours, at least 2 days, at least 4 days, at least 5 days, at least 7 days, at least 10 days, or at least 14 days. In some embodiments, the device components are configured and their amounts are selected so that the device provides an extended release of NO, to the cavity or surface of the subject, at a level of at least 10 ppm, at least 50 ppm, at least 100 ppm, at least 500 ppm, at least 1,000 ppm, at least 10,000 ppm over a period of at least 4 hours, at least 12 hours, or at least 24 hours. In some embodiments of the aforementioned extended release periods, the device components (e.g. nitrite source, proton source, gelling agent, viscosity modifier, etc.) and their amounts are selected so that the variation in the levels of NO varies is less than 2%, less than 5%, less than 10%, less than 20%, less than 30%, or less than 40%.

In some embodiments, the device components (e.g. the nitrite source, the gelling agent, the viscosity adjuster, the proton source and the optional thiol source) and their amounts are selected so that it increases a subject systemic or local NO level or plasma nitrite and/or nitrate level by at least 5%, at least 10%, at least 15%, at least 20%, at least 25%, at least 30%, at least 40%, at least 50%, at least 60% or more over a period of about 1 day, about 3 days, about 5 days, about 7 days, about 10 days, about 15 days, about 30 days or more in comparison with the NO level or plasma nitrite and/or nitrate level prior to administering the formulation. Various methods can be used for measuring the NO level or plasma nitrite and/or nitrate level, including for example the colorimetric method using the Griess reagent and the chemiluminescence method.

Another aspect of the patent document provides a kit, which includes a nitrite source, an optional proton source, and an optional thiol source, and a reservoir for loading these components. The reservoir is configured for application to a body cavity of a subject to treat a disease or condition. The scope of the components are as described above. The kit may further include instructions recorded in a tangible form for use of the components or the kit for treating a disease or condition by delivery of NO at a body cavity. In some applications, one or more components may be provided in pre-measured single use amounts in individual, typically disposable, patches, tubes or equivalent containers.

The kits or systems can also include instruction manuals and packaging materials for holding the container or combination of containers. Instructions, such as written directions or videotaped demonstrations detailing the use of the device for treating target diseases and conditions, can be included with the kit. Typical packaging materials for such kits and systems include solid matrices (e.g., glass, plastic, paper, foil, and the like) that hold the components in any of a variety of configurations (e.g., in a pouch, tube, and the like).

Nonlimiting exemplary combinations of different components in the device or the kit are provided below. Components in the same bracket are admixed with each other. Components not in the same bracket are physically separate from each other prior to the NO production or do not have substantive interaction for NO formation. (Abbreviations: H-honey, N-nitrite, RSH-thiol containing molecule (e.g., GSH, NAC), SHnp/mp-nano or microparticle with covalently attached thiol groups, RSHnp/mp-nano or microparticles with releasable thiol containing molecules (e.g., GSH, NAC), SNOnp/mp-nano or microparticle with covalently attached S-nitrosothiol groups, RSNOnp/mp-nano or microparticle with releasable molecules having S-nitrosothiol groups (e.g., GSNO, SNAC, SNAP), PEG (e.g., PEG400 and/or PEG200)

1. H+N with or without PEG
2. H+{PEG+N}
3. H+R–SH+N+PEG
4. H+{PEG+N+RSH}
5. {H+RSH}+{PEG+N}
6. {H+N}+{PEG+RSH}
7. H+{PEG+N+RSHnp/mp}
8. {H+RSHnp/mp}+{PEG+N}
9. {H+N}+{PEG+RSHnp/mp}
10. H+{PEG+N+SHnp/mp}
11. {H+SHnp/mp}+{PEG+N}
12. {H+N}+{PEG+SHnp/mp}
13. H+{PEG+N+RSNOnp/mp}
14. {H+RSNOnp/mp}+{PEG+N}
15. {H+N}+{PEG+RSNOnp/mp}
16. H+{PEG+N+SNOnp/mp}
17. {H+SNOnp/mp}+{PEG+N}
18. {H+N}+{PEG+SNOnp/mp}

In the device or kit disclosed in this patent document, the nitrite concentration after mixing with the gelling agent (e.g. Manuka honey) and optionally with other agent (e.g. viscosity adjuster such as PEG) can be modified depending on the intended use. In some embodiments, the concentration of the nitrite is more than 1 M, more than 2 M, more than 3 M, more than 4 M, more than 5 M, more than 6 M, or more than 7 M.

In an exemplary embodiment, a device or a kit (e.g. insert sponge, single or multiple layered bandage) containing (1) honey (e.g. Manuka honey) admixed with nitrite and (2) a thiol source (e.g. GSH or NAC) can be applied to skin for treating wound lesions. SNO is formed from both GSH and NAC in response to NO generation as moisture is pulled into the composition or kit (e.g. bandage).

Accordingly, different components of the kit may be in contact with each other or physically separate from each other. Depending on the specific configuration and the intended application, the kit may have 1, 2, 3 or more groups of components, where each group is not in direct contact with each other or the contact is insufficient to initiate the formation of NO. For instance, a sealed bandage may contain a mixture of honey, nitrite source and PEG and does not activate NO generation until being exposed to water or physiological environment in a subject. Alternatively, the nitrite may be mixed with PEG in one layer of the bandage and honey is impregnated in another layer, wherein the two layers have minimum interaction until pressed together and being exposed to a water or proton source, which can be present in a physiological environment (e.g., nose, ear, mucosa, gums, vagina, rectum) or available from an additional component of the kit.

Other non-limiting examples of the kit include single or multiple layered dressing, single or multiple layered film, sprayer or nebulizer, tube, cartridge, syringe, each of which contain the nitrite source, the gelling agent, and one or more of the above described components.

II. Method of Treating a Disease or Condition

Another aspect of the patent document provides a method of deliver NO systemically or locally to a subject. The method includes applying or placing the device described herein in a body cavity or a surface of the subject; and allowing the nitrite source and the proton source to react and generate a therapeutically effective amount of nitric oxide.

NO plays a key role in various biological pathways. For instance, it can supplement the reduced endothelial NO production, reduce activated macrophage population to avoid excessive tissue damage, restores normal macrophage population to support tissue repair, lower production of toxic reactive oxygen (ROS). In the context of preventing the pro-inflammatory cascade and resulting cytokine storm, NO restores normal balance of ACE/ACE2 and breaks the vicious circle of events caused by continuous depletion and decreased production of endogenous NO that contributes to the progressive damage from escalating inflammation. NO is also essential for maintaining/restoring crucial tissue perfusion and oxygenation caused by an uncontrolled cytokine storm. It prevents severe endothelial dysfunction, supplements diminished endothelial NO production; restores the natural ROS/NO balance, inhibits the cytokine storm and consequent far reaching systemic damage, prevents vascular endothelial and alveolar damage, inhibits platelet activation/sluggish blood flow, and maintains vital tissue perfusion.

By delivering NO systemically or locally, the method is applicable to the treatment of various diseases or conditions. Nonlimiting examples include pulmonary hypertension, skin/dermatological conditions (acne, inflammatory skin conditions, Raynaud's disease, pain, post herpetic lesions, shingles, infections (e.g. skin infections, catheter (IV catheters, urinary catheters, etc.) induced infections), inflammatory conditions, chronic rhinosinusitis, wounds, burns, leg ulcers (sickle cell, diabetic), onychomycosis, peripheral vascular disease, infected and/or inflamed mucosal tissues (periodontal disease, rectal/anal lesions, vaginal lesions), erectile dysfunction, female sexual dysfunction and vaginal infections/inflammation, catheter associated urinary tract infection, sinusitis, cystic fibrosis, acute respiratory distress syndrome, pulmonary fibrosis, chronic obstructive pulmonary disease (COPD), bronchiectasis, pulmonary infections including tb, pulmonary hypertension, and burns and other open wounds, inner and/or outer ear infections, gastric and intestinal diseases (ulcers, infections and inflammatory conditions), acute vascular inflammatory conditions (Hemorrhagic shock, Hemorrhagic fevers, Acute sickle cell crisis).

Suitable locations for applying the device include for example nose, nasal sinuses, ears, rectum, vagina, buccal cavity, and an open wound.

In some embodiments, the disease or condition treatable with the method include viral or bacterial infection, inflammation, neuropathic pain, sinusitis, cystic fibrosis, bronchiectasis, surgical or trauma induced wounds, vaginal deterioration, and sexual dysfunction.

A device such as a nasal sinus insert for post sinus surgery recovery provides enhanced wound recovery, prevents and treats infection, modulates inflammation, and controls neuropathic pain. Examples of treatment of chronic sinusitis include short term nasal insert to eliminate biofilms, reduce inflammation, eliminate pathogenic organism and restore normal NO production capability within the sinuses. Nasal inserts can also be used to the management of cystic fibrosis and bronchiectasis by producing a sustained level of NO that can be inhaled into the pulmonary system and either treat or prevent biofilm formation and the overgrowth of organisms such as Pseudomonas aurius. Nasal insert can also limits viral replication in the sinuses.

The device or method described herein can also be applied to the treatment of inner and outer ear infections. In most cases of inner ear infections cause fissures within the tympanic membrane thus allowing facile passage of infection fighting NO being generated by the insert within the ear canal. Additional examples include prevention and treatment of post myringotmy/tube implant infections which typically requires tube replacement. Similarly, an oral insert placed adjacent to the gum and cheek can release therapeutic levels of NO that reduces infection and inflammation associated with periodontal disease and prevents post dental procedure infections and inflammation. NO delivery via rectal inserts serves to accelerate the healing of surgical or trauma induced wounds including anal fissures.

Vaginal inserts are further examples for treating various diseases and conditions in women. Estrogen activity is mediated via the production of NO. NO releasing vaginal inserts could be a safer method that performs the same function as estrogen cream in terms of repairing age associated vaginal deterioration, increasing mucous production and facilitating sexual arousal (increase blood flow) in post menopausal women. Many women with a history of cancer are hesitant to use estrogen based therapeutics. The device and method of this patent document provide an effective alternative treatment regimen.

The device and method disclosed herein is also applicable to inhibition of biofilm growth. Biofilms are a major factor in creating drug resistance due to limiting drug access to the organisms and creating an interactive environment that facilitates the transmission of drug resistance through the community within the biofilm. Biofilms are also etiologic agents for a number of disease states in mammals. Otitis media, dental plaque, bacterial endocarditis, cystic fibrosis and Legionnaire's disease along with a broad array of hospital acquired, dental and medical clinic infections are examples of its pathology. Bacteria growing in biofilms display increased resistance to antibiotics. Commonly surveyed microbial organisms that form biofilms are *Burkholderia cenocepacia, Staphylococcus, Streptococcus, Pseudomonas,* and *Legionella* and their subtypes.

Further examples of the device and method disclosed herein include wound dressings/bandages capable of sustained NO release to address infection, biofilms, wound closure, and pain. NO generation can be initiated by moisture at the site of application or by external added proton source. The device can also be in the form of an insert, which is placed in a urinary catheter to provide urine-initiated sustained NO release to prevent catheter associated urinary tract infections.

The device and method are also capable of addressing pro-inflammatory insults including acute inflammatory insults triggered by certain viral infection (e.g., SARS CoV2, Dengue fever, and influenza), obesity and glucose induced inflammatory triggers, and inflammation triggered by exposure to toxic metals and chemicals. Non-specific antiviral effects of NO have been reported in a variety of viral infections, including HIV, vaccinia virus, enterovirus and coronavirus. NO delivery methods described herein can play a key role in multiple stages of COVID-19 prevention or therapy, including prevention of infection, intervention of mild patients, alternative rescue treatment of moderate and severe patients, and adjuvant treatment of mechanically ventilated patients. For instance, the device described herein provides an effective amount of NO for treating coronavirus (COVID-19) associated symptoms such as coughing and difficulty with breathing. Further, in patients with long COVID, side effects attributed to COVID that become manifest well after the seeming recovery from the primary infection include brain fog, fatigue, achiness, clotting issues, myocarditis, edema and more. Most of these symptoms can be attributed to a continued imbalance between pro-inflammatory and anti-inflammatory factors that favor development of and persistence of endothelial dysfunction. The device and method disclosed herein can be applied to the treatment of COVID infections as well as clinical manifestations of long COVID.

The device disclosed herein can also be applied to a surface of a subject to treat diseases or conditions including for example burns and leg ulcers (sickle cell, diabetic). Additional agents such as antioxidants, antibiotics, antifungal agents, and/or preservatives can also be included in the reservoir to prevent infection or promote healing. Application of the device the surface area can also prevent or reduce the risk of infection.

In some embodiments, the method disclosed herein includes a step of lowing the temperature of the device or one or more or all components (e.g., proton source, nitrite source, thiol source and SNO source) prior to application of the device in order to improve the storage stability and/or control the release and timing of NO upon application. The temperature of the device or one or more or all components (e.g., proton source, nitrite source, thiol source and SNO source) prior to application may range from about −50° C. to about 30° C., from about −30° C. to about 20° C., from about −20° C. to about 10° C., from about −20° C. to about 0° C., from about −20° C. to about 5° C., from about −20° C. to about −10° C., from about −10° C. to about 10° C., or from about −10° C. to about 0° C. Non-limiting examples of the temperature prior to application include about −30° C., −20° C., −15° C., −10° C., −5° C., 0° C., 5° C. and 10° C.

Temperature control thus allows for the preparation of highly stable devices (e.g. pads, inserts, etc) that can be stored in a refrigerator or cooled down to a certain temperature and then deployed and applied when needed. For instance, PEG400 (a solid at or below 4° C.) can be mixed with a nitrite source (salts or in particles) and/or NAC to form a stable solid with no evidence of NO release at 4° C. or colder. The nitrite and NAC controls the amount of NO that can be released. These components do not have to dissolve in the PEG as they can form a frozen suspension. When exposed to water, the components will mix and dissolve with time. Alternatively, upon warming and exposure to moisture/aqueous solvents, the solid mixture slowly dissolves and releases NO.

The device and method described herein can be practiced before clinical symptom of a disease or condition is detected in order to prevent or reduce the risk of the disease or condition. For example, the device such as a nasal inert can be used prophylactically to prevent or reduce risk of viral infection or severe symptoms.

The method allows for a sustained generation of NO and thus provides maximum effects for various medical or sanitary needs. In some embodiments, an effective amount of NO is released over a period of more than 5 minutes, more than 10 minutes, more than 20 minutes, more than 40 minutes, more than 60 minutes, more than 90 minutes, more than 2 hours, more than 3 hours, more than 4 hours, more than 6 hours, more than 12 hours, more than 18 hours, or more than 24 hours.

As will be readily apparent to one skilled in the art, the useful in vivo dosage to be administered and the particular mode of administration will vary depending upon the age, weight and mammalian species treated, the particular agents or components employed, and the specific target use. The determination of effective dosage levels, that is the dosage levels necessary to achieve the desired result, can be accomplished by one skilled in the art using routine pharmacological methods (see e.g., Fingl et al. 1975, in "The Pharmacological Basis of Therapeutics", which is hereby incorporated herein by reference in its entirety, with particular reference to Ch. 1, p. 1). Typically, human clinical applications of products are commenced at lower dosage levels, with dosage level being increased until the desired effect is achieved.

Dosage amount and interval may be adjusted individually to provide a desirable NO level. The level may vary for each device or kit but can be estimated from in vitro data. Dosages necessary to achieve the target NO level will depend on individual characteristics and route of administration. However, HPLC assays or bioassays can be used to determine plasma concentrations of released NO. The dosage and frequency of administration may be dependent on the subject being treated, on the subject's weight, the severity of the disease, the manner of administration and the judgment of the prescribing physician.

EXAMPLES

Example 1

Generation of NO. Equivalent amounts of a mixture of nitrite loaded particles+NAC were added to two separate tubes. Tube 1 was filled with water and Tube 2 was filled with the same volume of solvent as for tube 1 but the solvent was a mixture of PEG400 with water (50/50 by volume). Tube 1 turned red immediately and began to bubble very shortly after combining the dry powder with the water. Tube 2 turned red much more slowly but eventually turned the same red color as in tube 1 and exhibited robust bubbling.

Example 2

NO generation from a PEG400 soaked sponge loaded with nitrite-particles in the presence of a thiol source. Nasopore sponge was pushed and compacted into the bottom of a tube. PEG400 was then added. When the sponge was saturated with PEG400, a dry mix of nitrite loaded particles and NAC was mixed into the PEG soaked sponge. After an excess of water was added, the sponge began to progressively develop a red color throughout the matrix consistent with SNO-NAC formation. No color change was observed prior to addition of water. Bubbling from all parts of the sponge was observable. The red color was confined to the sponge. Bubbling persisted for over 24 hours. As the NO is released from the SNO-NAC the sponge progressively loses the red color.

Example 3

Controlled release of NO with viscosity adjuster and nitrite loaded particles under low temperature. Two samples of solid refrigerated blocks of PEG, nitrite and NAC was inserted into an excess of water. One sample contained nitrite loaded particles and the other sample contained nitrite salt. The insertion into water initiated the formation of the red color (SNO-NAC) and the continuous release of NO bubbles over a 20 hour period. The PEG layer remained relatively intact over this period and limits release of the SNO-NAC. The sample with the nitrite particles appeared to progress more slowly.

Example 4

Preparation of nasal sponge and testing of NO release. The following dry mix consisting of the nitrite source and a thiol source were added to a fixed volume of solvent and then immediately added to an absorbent reservoir. A nitrite salt (140 mg) as the nitrite source and NAC as the thiol source were mixed with water (1 ml) and then added to the sponge (Stryker Nasopore) which completely absorbed the liquid.

Variations of this experiment were examined for longer NO release time. Solvents containing water with Manuka honey or PEG400 were used as proton source and nitrite loaded particles and thiol doped particles (either covalently attached thiols or NAC loaded particles) served as NO releasing materials. A sponge insert loaded with the mixture provided about 3.8 ppm of NO over a period of 12 hours.

Example 5

Test of bandage loaded with nitrite source for NO release. A bandage was loaded with nitrite particles and a second bandage contained nitrite particles admixed with NAC. Both bandages had manuka honey mixed with the nitrite source. The bandages were attached to the front arm of a test individual. After an hour, the bandage loaded with nitrite particles and NAC turned red but the other did not change color. The bandages was removed after 3 hours. It could be seen that the region of the bandage loaded with nitrite particles and NAC was bright red. The addition of a small amount of water resulted in bubbling from the red region. The skin under the red region was pink even after washing off any remaining honey.

Example 6

Reservoir loaded with frangible or dissolvable (water soluble) units containing nitrite source and/or other components. A hygroscopic sponge was embedded with a capsule or frangible pouch where the embedded entity contained materials that generate and release NO upon uptake of water into the sponge. Variations of the device include multiple capsules or pouches or divided capsules to allow for different components (e.g. NO releasing dry components in one chamber and viscogenic solvents such as Manuka honey or PEG400 in another) to remain separated until water activation or crush initiated mixing (with frangible pouch(s)). The capsules dissolved when they contacted water. The hygroscopic sponge materials tested from Stryker rapidly absorbed the various liquid solvent including honey and PEG400 resulting in a uniform distribution within several minutes. These loaded sponges were then tested by insertion into a tube and covered with water. The color changes and bubbling of NO released gas was then monitored. The red color is an indication of S-nitrosothiols formation. This same scheme can be modified to accommodate NO releasing wound coverings.

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of the device, or a step of the method, and may result from a different combination of described components, or that other un-described alternate embodiments may be available for a device, kit or method, is not to be considered a disclaimer of those alternate embodiments. It will be appreciated that many of those un-described embodiments are within the literal scope of the following claims, and others are equivalent.

The invention claimed is:

1. A method of treating a disease or condition in a subject, comprising:
   (a) placing a device in a body cavity or a surface of the subject in need thereof,
      wherein the device comprises:
      a nitrite source entrapped within honey;
      a reservoir for loading the nitrite source and configured for being applied to the body cavity or the surface of the subject;
   (b) contacting the nitrite source with a proton source to generate a therapeutically effective amount of nitric oxide (NO).

2. The method of claim 1, wherein the nitrite source and the proton source are separately stored in the device prior to the device being applied to the body cavity.

3. The method of claim 1, wherein the proton source is physically separate from the device.

4. The method of claim 1, wherein the nitrite source comprises an alkali metal nitrite, an alkaline earth metal nitrite, a transition metal nitrite, an ammonium nitrite or any combination thereof.

5. The method of claim 1, wherein the nitrite source comprises nitrite loaded nanoparticles.

6. The method of claim 1, wherein the proton source is water.

7. The method of claim 1, wherein the reservoir is further loaded with a thiol source admixed with the nitrite source.

8. The method of claim 7, wherein the source of thiol group is thiol-containing molecules.

9. The method of claim 7, wherein the thiol source is thiol-containing nanoparticles, which have the thiol groups covalently attached thereto.

10. The method of claim 1, further comprising a source of S-nitrosothiol (SNO) group admixed with the nitrite source.

11. The method of claim 1, wherein the nitrite source comprises an immediate release portion and an extended release portion.

12. The method of claim 1, wherein the disease or condition is viral or bacterial infection, inflammation, neuropathic pain, sinusitis, cystic fibrosis, bronchiectasis, surgical or trauma induced wounds, vaginal deterioration, and sexual dysfunction.

13. The method of claim 1, wherein the body cavity is nose, nasal sinuses, ears, rectum, vagina, mucosa surface in the mouth, or an open wound.

14. The method of claim 1, wherein the device is inserted into the nostril of the subject to treat chronic sinusitis, neuropathic pain, cystic fibrosis or bronchiectasis.

15. The method of claim 1, wherein the device is inserted into the nostril of the subject or the ear of the subject to treat inner or outer ear infection.

16. The method of claim 1, wherein the device is applied to the subject prophylactically.

17. The method of claim 1, wherein the reservoir is a sponge or a patch.

18. The method of claim 1, wherein the honey is admixed with PEG.

19. The method of claim 18, wherein the amounts of the honey and the PEG are selected to provide an extended release of the therapeutically effective amount of the NO over a period of at least 24 hours.

20. The method of claim 1, wherein the honey is substantially free from water.

21. The method of claim 7, wherein the source of thiol is N-acetyl cysteine (NAC).

* * * * *